US010352770B2

(12) United States Patent
Morales Rodriguez et al.

(10) Patent No.: US 10,352,770 B2
(45) Date of Patent: Jul. 16, 2019

(54) OPTICAL SPECTROSCOPY SYSTEM AND METHOD FOR MONITORING LIQUID PHASE CHEMICAL REACTIONS

(71) Applicant: UT-Battelle, LLC, Oak Ridge, TN (US)

(72) Inventors: Marissa E. Morales Rodriguez, Knoxville, TN (US); Joanna McFarlane, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 15/790,872

(22) Filed: Oct. 23, 2017

(65) Prior Publication Data
US 2018/0113025 A1    Apr. 26, 2018

Related U.S. Application Data

(60) Provisional application No. 62/411,010, filed on Oct. 21, 2016.

(51) Int. Cl.
*G01J 3/42*  (2006.01)
*G01J 3/44*  (2006.01)
(Continued)

(52) U.S. Cl.
CPC ................... *G01J 3/42* (2013.01); *G01J 3/44* (2013.01); *G01N 21/25* (2013.01);
(Continued)

(58) Field of Classification Search
CPC ........ G01J 3/42; G01J 3/44; G01J 5/20; G01J 5/10; G01N 21/25; G01N 21/3504;
(Continued)

(56) References Cited

U.S. PATENT DOCUMENTS 5,416,579 A  *  5/1995  Barshad  ...............  G01N 21/552
356/300
7,102,751 B2    9/2006  Harper
(Continued)

OTHER PUBLICATIONS

Pengel et al.: "Attenuated total reflection mid-IR-spectroscopy for electrochemical applications using a QCL", Lasers, Sources, and Related Photonic Devices Technical Digest, 2012 OSA.
(Continued)

*Primary Examiner* — Jamil Ahmed
(74) *Attorney, Agent, or Firm* — Fox Rothschild LLP (57) ABSTRACT

A system for monitoring a chemical reaction in a liquid reactor system includes a sample liquid conduit in communication with the liquid reactor system for receiving sample liquid and directing the sample liquid to an optical spectroscopy device, and a laser beam source. The optical spectroscopy device receives the laser beam from the laser source, and guides the laser beam to the sample liquid to generate an optical spectroscopy signal. A detector detects the optical spectroscopy signal and creates a detection signal responsive to the optical spectroscopy signal. A processor processes the detection signal to determine the identity and amount of at least one chemical species in the liquid. A system for continuously sampling a chemical reaction and a method for continuously monitoring and controlling a chemical reaction are also disclosed.

12 Claims, 6 Drawing Sheets

(51) Int. Cl.
G01N 21/25 (2006.01)
G01N 21/39 (2006.01)
G01N 21/65 (2006.01)
G21C 17/00 (2006.01)
G01N 21/956 (2006.01)
G01N 21/3504 (2014.01)
G01N 21/552 (2014.01)
G01N 21/75 (2006.01)
G01N 21/84 (2006.01)

(52) U.S. Cl.
CPC ......... *G01N 21/3504* (2013.01); *G01N 21/39* (2013.01); *G01N 21/552* (2013.01); *G01N 21/65* (2013.01); *G01N 21/956* (2013.01); *G21C 17/00* (2013.01); *G01N 21/75* (2013.01); *G01N 2021/8411* (2013.01)

(58) Field of Classification Search
CPC ...... G01N 21/39; G01N 21/552; G01N 21/65; G01N 21/956; G01N 21/75; G01N 33/00; G01N 2021/8411; G21C 17/00; G01V 5/08
See application file for complete search history.

(56) References Cited

U.S. PATENT DOCUMENTS

| | | | |
|---|---|---|---|
| 7,812,312 B2 | 10/2010 | Mantele et al. | |
| 8,445,841 B2 | 5/2013 | Szobota et al. | |
| 8,502,148 B2 | 8/2013 | Wagner et al. | |
| 9,041,923 B2 | 5/2015 | Messerchmidt | |
| 2004/0202573 A1* | 10/2004 | van den Brink | B01J 19/0046 506/38 |
| 2010/0181472 A1* | 7/2010 | Csutak | E21B 47/10 250/269.1 |
| 2011/0150734 A1* | 6/2011 | Kumakiri | B01J 10/007 423/245.1 |
| 2012/0181431 A1* | 7/2012 | Mitin | G01N 21/3581 250/338.4 |
| 2016/0116407 A1 | 4/2016 | Ben-Zion et al. | |
| 2016/0209325 A1 | 7/2016 | Kotidis et al. | |
| 2016/0258863 A1 | 9/2016 | Pastore et al. | |
| 2016/0272519 A1* | 9/2016 | Ledwell | C02F 3/006 |

OTHER PUBLICATIONS

Buscher et al.: "Raman Spectroscopic Study of the Aging and Nitration of Actinide Processing Anion-Exchange Resins in Concentrated Nitric Acid", Applied Spectroscopy, vol. 53, No. 8, 1999.
van Staden et al.:Kinetic Study of the Decomposition of Nitrite to Nitrate in Acid Samples Using Raman Spectroscopy, Applied Spectroscopy, vol. 50, No. 8, 1996.
Ianoul et al.: "UV Resonance Raman Spectroscopic Detection of Nitrate and Nitrite in Wastewater Treatment Processes", Anal. Chem 2002, 74, 1458-1461.
Recommendations on the Transportation of Dangerous Goods, Manual of Tests and Criteria, Fourth Edition, United Nations, New York and Geneva, 2003.
Gowland et al.: "", Journal of Inorganic nuclear Chemistry vol. 43, No. 11, pp. 2859-2862, 1981.
Morales et al.: "Infrared microcalorimetric spectroscopy using quantum cascade lasers", Optics Letters 38(4):507-9—Feb. 2013.
Giguere et al.: Infrared Spectrum, Molecular Structure and Thermodynamic functions of hydroxlamine:, Can J. Chem, 1952, 30, 948.
Armbuster et al.: "Limit of Blank, Limit of Detection and Limit of Quantitation", Clin Biochem Rev, 2008, 29, Suppl (1), S49-S51.
Long et al.: "Limit of Detection", Anal. Chem 1952, 30, 948.
Li et al., "A novel hydroxylamine ionic liquid salt resulting from the stabilization of NH2OH SO3Hfunctionalized ionic liquid" Chem Communication, 2015, 1930.
Marziano et al.: "On-Line Mid-IR Spectroscopy as a Real-Time Approach in Monitoring Hydrogenation Reactions" Organic Process Research, 2000, 357-361.
Koch et al.: "Ultrasound-Enhanced Attenuated Total Re?ection Mid-infrared Spectroscopy In-Line Probe: Acquisition of Cell Spectra in a Bioreactor", Analytical Chemistry, 2015, 2314-2320.
McFarlane et al.: "Hydroxylamine Nitrate Decomposition Under Non-radiological Conditions", ORNL, Jul. 2015.
Alcaraz et al.:External-Cavity Quantum Cascade Laser Spectroscopy for Mid-IRTransmission Measurements of Proteins in Aqueous Solution, Analytical Chemistry, 2015, 87, 6980?6987.
Jouy et al.: "Mid-infrared spectroscopy for gases and liquids based on quantum cascade technologies", Analyst, 2014, 139, 2039.
Mizaikoff: "Waveguide-enhanced mid-infrared chem/bio sensors", Chem. Soc. Rev., 2013, 42, 8683.
Brandsetter et al.: "Tunable external cavity quantum cascade laser for the simultaneous determination of glucose and lactate in aqueous phase", Analyst, 2010, 135, 3260-3265 | 3261 Published on Nov. 2, 2010. Downloaded by University of Tennessee at Knoxville on Oct. 13, 2017 17:58:04. View Article Online.
Haase et al.: "Advancements in quantum cascade laser based infrared microscopy of aqueous media" The Royal Society of Chemistry 2016 , DOI: 10.1039/c5fd00177c.
Van Neste et al.: "Standoff Spectroscopy of Surface Adsorbed Chemicals" Anal. Chem., 2009, 81 (5), pp. 1952-1956.
Schaden et al.: "Simultaneous measurement of two compounds in aqueous solution with dual quantum cascade laser absorption spectroscopy", Appl. Phys. B 83, 135-139 (2006).
Morales-Rodriguez et al.: "Standoff imaging of chemicals using IR spectroscopy", Proceedings of the SPIE, vol. 8031, id. 80312D (2011).
Morales-Rodriguez et al.: "Infrared microcalorimetric spectroscopy using quantum cascade lasers" Opt Lett. Feb. 15, 2013;38(4):507-9.
Ernest H. Braue et al.:"Consistency in Circle Cell FT-IR Analysis of Aqueous Solutions", Applied Spectroscopy vol. 41, Issue 6 <https://www.osapublishing.org/as/issue/cfm?volume=41&issue=6>, pp. 1057-1067 (1987).

\* cited by examiner

OPTICAL SPECTROSCOPY SYSTEM AND METHOD FOR MONITORING LIQUID PHASE CHEMICAL REACTIONS

CROSS-REFERENCE TO RELATED APPLICATIONS

This application claims priority to U.S. Provisional Patent Application No. 62/411,010 filed Oct. 21, 2016, entitled "Quantum Cascade Laser Mid-Infrared Spectroscopy for Online Monitoring of Aqueous Chemical Processing", the entirety of which is incorporated herein by reference.

STATEMENT REGARDING FEDERALLY SPONSORED RESEARCH

This invention was made with government support under contract no. DE-AC05-000R22725 awarded by the US Department of Energy. The government has certain rights in this invention.

FIELD OF THE INVENTION

The present invention relates to optical laser spectroscopy for chemical processing, and more particularly to online monitoring and control of chemical reactions in liquid phase.

BACKGROUND OF THE INVENTION

The utility of standoff detection of molecules has been demonstrated in the solid and gas phase, for example methane in field experiments and in the detection of explosive dust collected on solid surfaces. However, many chemical processes occur in solution phase, and involve a number of different molecules with similar functional groups. Vibrational spectra of species in solution can be interpreted to give thermal energies of IR-active compounds, allowing these to be included in chemical kinetic and dynamical models. In aqueous solution, there are two issues that need to be addressed, the high background and spectral selectivity. Hence, Raman is usually the method of choice for vibrational spectroscopy as it avoids background absorption from $H_2O$. Because of selection rules, Raman is generally much less sensitive than IR absorption, unless methods such as surface enhanced Raman are used. Raman has been used to monitor the degradation of anion-exchange resins used for the separation of plutonium isotopes in highly acidic conditions. Because this method depends on far UV excitation; however, this method becomes unfeasible for use in applications involving high concentrations of nitrate because self absorption becomes problematic at concentrations above 3.5 mM. The detection limit for such methods have been reported at concentrations range of few milligrams per liter.

SUMMARY OF THE INVENTION

A system for online monitoring a chemical reaction in a liquid reactor system includes a sample liquid conduit in communication with the liquid reactor system for receiving sample liquid and directing the sample liquid to an optical spectroscopy device. The optical spectroscopy device receives the laser beam from a laser source, and guides the laser beam to the sample liquid to generate a specific absorption signal related to the sample liquid, the optical spectroscopy signal. A detector detects the modified laser light and creates a detection signal responsive to the optical spectroscopy signal. A processor processes the detection signal to determine the identity and amount of at least one chemical species in the liquid. The liquid reactor system can be part of a nuclear reactor system.

The optical spectroscopy device can include a liquid cell attenuated total reflectance (ATR) device and the optical spectrometry signal is an absorption signal. The optical spectroscopy device can include a liquid chamber for receiving the sample liquid and transmitting the laser beam to the liquid. The laser beam source can include a quantum cascade laser (QCL) source. The laser beam has a wavelength, and a portion of the liquid chamber can be transmissive to the wavelength of the laser beam. The laser beam source can provides a laser beam having a wavelength between 3.7 and 12.5 µm. The system can further include a device for generating a time signal, and correlating the time signal with the detection signal and with the amount of at least one chemical species at a time the sample liquid was processed.

A system for controlling chemical reactions in liquid reactor systems can include a sample liquid conduit in communication with the liquid reactor system for receiving sample liquid and directing the sample liquid to an optical spectroscopy device. A laser beam source is provided. The optical spectroscopy device receives the laser beam from the laser beam source, and guides the laser beam to the sample liquid to generate an optical spectroscopy signal. A detector detects the optical spectroscopy signal and creates a detection signal responsive to the optical spectroscopy signal. A processor processes the detection signal to determine the identity and amount of at least one chemical species in the sample liquid and generates at least one process control signal responsive to the amount of the at least one chemical species in the liquid reactor system. At least one process controller is provided for controlling at least one process control device of the chemical reaction responsive to the process control signal.

A method for monitoring a chemical reaction in a liquid reactor system, includes the step of directing a sample liquid stream from the liquid reactor system to an optical spectroscopy device. A laser beam is generated and directed to the optical spectroscopy device, and guided to the sample liquid to generate an optical spectroscopy signal. A detector creates a detection signal responsive to the optical spectroscopy signal. The detection signal is directed to a processor, and processed to determine the identity and amount of at least one chemical species in the liquid system. The processor can process the identity and amount of the at least on chemical species to generate at least one process control signal. The process control signal can be directed to a process controller to control at least one process control device of the liquid reactor system. The method can be continuous.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

A system for monitoring a chemical reaction in a liquid reactor system includes a sample liquid conduit in communication with the liquid reactor system for receiving sample liquid and directing the sample liquid to an optical spectroscopy device. The optical spectroscopy device receives the laser beam from the laser source, and guides the laser beam to the sample liquid to generate a specific absorption signal related to the sample liquid, the optical spectroscopy signal. A detector detects the modified laser light and creates a detection signal responsive to the optical spectroscopy signal. A processor processes the detection signal to determine the identity and amount of at least one chemical species in the liquid. A system for controlling a chemical reaction and a method for monitoring and controlling a chemical reaction are also disclosed.

In one embodiment, the optical spectroscopy device comprises an attenuated total reflectance (ATR) device and the optical spectrometry signal can be an evanescent wave absorption signal. In the ATR, a crystal made of compatible material (including but not limited to germanium, zinc selenide or diamond) creates an evanescent wave as the laser beam propagates. The evanescent wave is in contact with the sample where specific wavelengths are absorbed. For sampling the apparatus uses a liquid cell connected to the liquid stream from the reactor. A liquid cell can include attenuated total reflection cell, or customized spectroscopic cell with a material transparent to the laser light. Depending on the chemical reaction under investigation the materials can include but not limited to zinc selenide, germanium, quartz, and/or diamond. A material that is not reactive with the chemical system.

The apparatus uses optics and a photodetector to translate the photon count after the laser light is in contact with the sample to an electrical signal for light attenuation monitoring.

The optical spectroscopy device can be a liquid chamber for receiving the sample liquid from a chemical reactor and transmitting the laser beam to the liquid via liquid cell. The laser beam can have single or multiple wavelength, that is propagated through the liquid chamber that is transmissive to the wavelength or wavelengths of the laser beam.

The laser beam source can be any suitable laser beam source. In one embodiment the laser beam source is a quantum cascade laser (QCL) source.

The laser beam source can provides a laser beam having a wavelength between 200 nm and 12 μm]. In one embodiment, the wavelength is mid-IR or between 3.7 and 12.50 μm. The invention can be used to effectively monitor the redox states of the actinides and key species such as $NO_3-$ and $HNO_2$. Mid-IR is sensitive to the detection of many other chemical species, such as those containing nitrate, sulfate, and carbonate anions, or IR active cations such as the ammonium cation. The laser beam wavelength is selected to provide optical molecular excitation for the chemical species of interest. Mid IR is desirable because mid infrared excels in selectivity and sensitivity as its wavelengths are absorbed by specific molecular bonds of selectivity for many molecules, but other sources of light can include near infrared and ultraviolet. Multiple or single wavelengths can also be employed. The laser peak power can be selected for the operating characteristics of the system, and can be >150 mW.

The detector can be selected to detect the optical spectroscopy signal that is generated by the laser source in the optical spectroscopy device. The photodetector can include, mercury cadmium telluride detector with detectivity, $D^*$, higher or equal to $4.5 \times 10E8$ at optimum wavelength for infrared laser sources. Other photodetectors, such as but not limited to photodiodes, photomultipliers tubes, can be used depending on the wavelength of the laser source used. In one embodiment, the detector can be a high sensitivity, compact and thermoelectrically cooled detector to continuously monitor the changes in amplitude by specific wavelengths of the laser beam. The thermoelectrically cooled detector does not require special conditions for operation, such as water or liquid nitrogen cooling, and, thus, makes an overall compact system. The changes in amplitude are translated to volts and are specific to the absorption of the sample flow from the reactor.

The system can include a device for generating a time signal. The time signal can be correlated with the detection signal. The information can be used to record the progress of the reaction with time.

A system for controlling chemical reactions in liquid reactor systems, can include a processor for processing the detection signal to determine the identity and amount of at least one chemical species in the sample liquid and generating at least one process control signal responsive to the amount of the at least one chemical species in the liquid reactor system. A process controller can be provided for controlling at least one process control device of the chemical reaction responsive to the process control signal.

A method for monitoring a chemical reaction in a liquid reactor system, includes the step of directing a sample liquid stream from the liquid reactor system to an optical spectroscopy device. A laser beam is generated. The laser beam is directed to the optical spectroscopy device, and guided to the sample liquid to generate an optical spectroscopy signal. A detector creates a detection signal responsive to the optical spectroscopy signal. The detection signal is then directed to a processor. The processor processes the detection signal to determine the identity and amount of at least one chemical species in the liquid system.

The processor in one embodiment processes the identity and amount of the at least on chemical species to generate at least one process control signal. The at least one process control signal can be directed to a process controller to control at least one process control device of the liquid reactor system.

The processor can continuously and remotely acquiring data from the detector. Data will continuously be analyzed using software with a built in library with the absorption patterns of the chemicals of interest. The software can include but not limited to pattern recognition algorithms, chemometrics, partial least square analysis, for example. The method can be continuous, providing for continuous monitoring and control of the reactor system. The software can alert the operator of reaction progress and abnormal conditions, should they arise.

The invention provides the capability to perform online and real time monitoring of an active system as a chemical reaction in water is taking place. Online data and control information transmission can be enabled using suitable and known internet and wireless technology. The sampling is done by establishing a liquid stream from the reactor to the optical spectroscopy device and back to the reactor, thus minimizing exposure of the electronics and operator to hazardous conditions including, ambient, chemical and or radiological. The data analytics can be sent to the control systems (SCADA) for real time information of the chemical reaction progress. In the example case, a redox reaction was monitored. The apparatus combines an attenuated total reflection cell and infrared tunable external cavity quantum cascade lasers.

The system can send an electrical trigger pulse to the laser control to start data collection and wavelength tuning to make a detection and provide an answer on chemical detection and extrapolate concentration in about 100 milliseconds. Fourier transform model can be used to extract the laser wavelength information as a function of time. Chemical information is derived by combining but not limited to chemometrics, pattern recognition algorithms and machine learning.

The system is capable of detecting and identifying the chemicals of interest at low concentrations in aqueous and organic solution with high sensitivity and selectivity, offered by the Mid-IR QCL. The system provides wide dynamic range, portability, flexibility, and can be deployable at a location close to a shielded chemical reactor or "hot cell".

Figure 1:
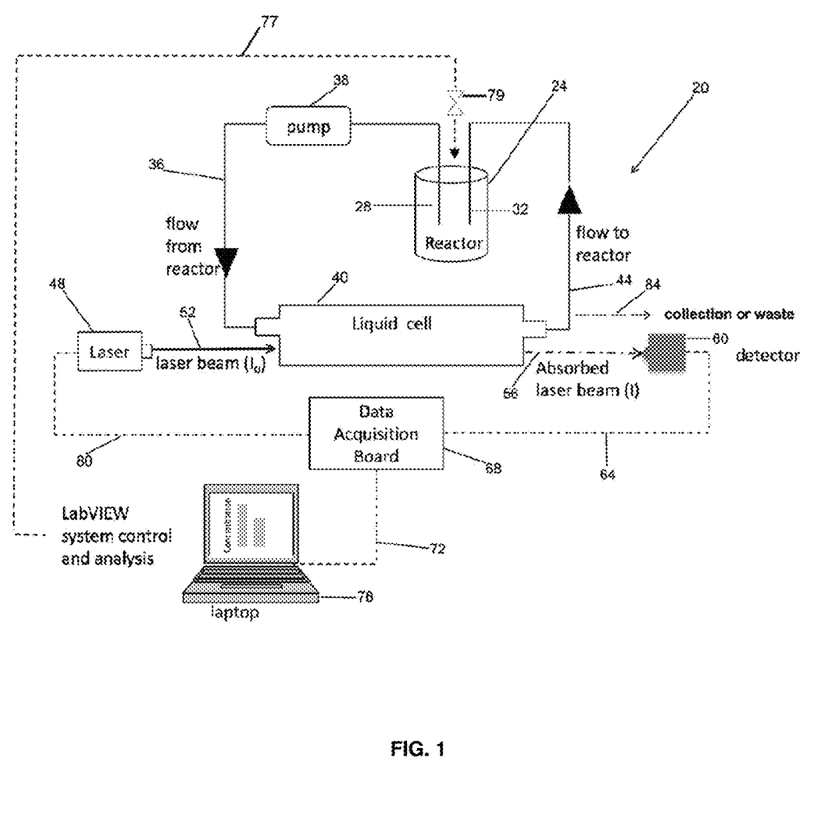
FIG. 1 is a schematic diagram of a system according to the invention.

A suitable monitoring system 20 according to the invention is shown if FIG. 1. The system 20 includes a liquid reactor system 24 having a sample fluid outlet 28 and possibly also a sample fluid inlet 32. A sample fluid conduit provides for flow of a sample fluid side stream 36, which can be assisted by suitable structure such as a pump 38. The sample fluid flows into an optical spectroscopy device such as the sample liquid chamber or cell 40. A laser beam source 48 generates a laser beam 52 which is transmitted through the liquid chamber or cell 40 to generate an optical spectroscopy signal 56. The optical spectroscopy signal 56 is directed to a detector 60. The detector 60 produces a detection signal 64 which is transmitted to a processor 76, which can be through a data acquisition board 68. The processor can be used to continuously monitor the reaction as a function of time, or through a suitable control line 77 to control one or more process control devices illustrated schematically by the valve 79 used to control reactant flow, but can also be a suitable process device to control other variable such as temperature, pressure, reactant flow in or out of the reactor, and the like. The sample fluid can then be returned to the reactor 24 through return line 44 and reactor sample fluid return inlet 32, or alternatively the sample fluid can be sent to waste or collection through exhaust line 84.

Figure 2:
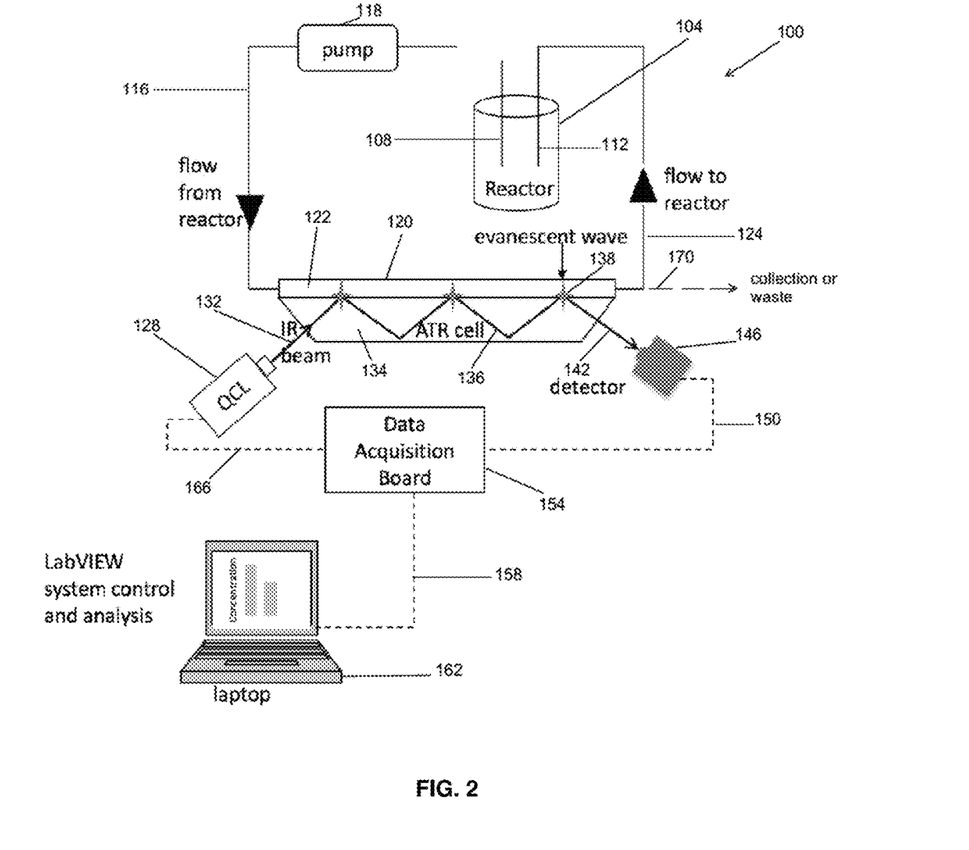
FIG. 2 is a schematic diagram of a QCL-ATR system according to the invention.

In another embodiment, to monitor a chemical process a liquid flow can be established between the reactor vessel and the ATR cell. As the liquid flow passes across the crystal of the ATR cell, a QCL IR beam propagates through the ATR cell crystal generating an evanescent wave that is in contact with the solution, as shown in FIG. 2. The system 100 includes a liquid reactor system 104 having a sample fluid outlet 108 and possibly also a sample fluid inlet 112. A sample fluid conduit provides for flow of a sample fluid side stream 116, which can be assisted by suitable structure such as a pump 118. The sample fluid flows into a ATR optical spectroscopy device 120 having a liquid chamber or cell 122. A laser beam source 128 generates a laser beam 132 which enters the ATR 134 creating an evanescent wave 138 which contacts sample fluid flowing through the liquid chamber or cell 122. This interaction affects the reflectance transmission 136 of the laser beam through the ATR 134, and generates an optical spectroscopy signal 142. The optical spectroscopy signal 142 is directed to a detector 146. The detector 146 produces a detection signal 150 which is transmitted to a processor 162, which can be through a data acquisition board 154. The processor can be used to continuously monitor the reaction, or through a suitable control line to control one or more process control devices. The sample fluid can then be returned to the reactor 104 through return line 124 and reactor sample fluid return inlet 112, or alternatively the sample fluid can be sent to waste or collection through exhaust line 170.

A commercially available ATR cell from Pike Technologies, Madison, Wis., was used. The ATR cell model used allows a flow of liquid across the crystal, as desired, and also permits introduction of light from a non-standard source (i.e., the QCL). In addition, the temperature in the ATR work plate can be controlled to maintain a stable temperature from the reaction vessel to the ATR where chemical identification is performed. The QCL beam is internally reflected 10 or 20 times, depending on the crystal, and the changes in the intensity of the IR light per wavelength is associated with absorption of the liquid sample.

The QCL system has four laser Modules with wavelength tuning ranges of 3.77-4.49 µm and 6.87-12.50 µm. The broadly tunable wavelength range allows the system to cover multiple spectral absorption features or peaks of the chemicals of interest, increasing the sensitivity and selectivity to identify different chemicals in a mixture. A characteristic absorption spectrum is generated using the signal from the detector and the wavelength signature of the QCL. In this case the absorption spectrum of each nitrate/nitrite species is unique and therefore gives a definitive fingerprint for molecular identification. Using this prototype, chemical identification is performed by the attenuation at specific wavelengths of the QCL IR beam coming out of the ATR cell. The beam is directed onto an MCT detector from VIGO, Ozaraw Mazowiecki, Poland systems model PCI-3TE. The MCT is a compact three stage thermoelectrically cooled detector optimized to provide high performance in the spectral range from 2 to 13 µm, $D^* \geq 4.5 \times 10^8$ at $\lambda_{opt}$. The QCL sources are broadly tunable, pulsed (Daylight Solutions, CA), and provide peak power of up to 400 mW.

The QCL module is operated in a pulsed mode of 500 ns, 100 kHz repetition rate, 5% duty cycle and a scan speed of 0.5 µm/sec. A National Instruments LabVIEW, Austin, Tex. interface communicates with the QCL module to control the start/stop of the wavelength scan, data collection, display and storage. The data is collected using the multifunctional data acquisition NI USB-6251 BNC from National Instruments, Austin, Tex. The laser module sends a trigger pulse to the data acquisition board to begin data capture of each wavelength scan. The start and stop of each scan is determined by the time required for each laser module to tune through its wavelength range. As the QCL emits tuning wavelengths, the LabVIEW interface collects the output voltage from the detector as a function of time. The output voltage of the detector is directly related to the intensity or attenuation of the QCL source per wavelength.

The LabVIEW interface uses a Fourier transform to extract the spectral information from the data collected as a function of time. The total time from start to end to acquire one spectrum is about 45 seconds with a resolution of 0.6 to 2 nm. The spectral resolution of this system is 3 orders of magnitude better than reported systems for online FTIR spectroscopy.

Examples of applications of the present invention can include aqueous processing of biomaterials, as organic acids and other functionalized organics produced in these processes have strong spectral absorptions in the IR.

In a miniaturized form, the invention can be package to be used in the field. The lasers can be supported by battery power and the optical alignment can be locked down to allow use in the field. The invention can be used to monitor water for contamination from the chemical or mining industries as well as agricultural run off for nitrates and phosphates, and military installations for perchlorate contamination. In these cases, the apparatus can be configured for high sensitivity, involving a multipass cell.

ATR attachments coupled with Fourier Transform IR Spectroscopy (FTIR) allow measurement of chemical species in aqueous solution or solids; however, the sensitivity of the QCL light sources is much higher because of the intensity and collimation of the IR.

The monitoring of chemical processing in hazardous or extreme conditions challenges methods that rely on sampling followed by off-line analysis. Continuous processes with reactive species are particularly difficult to control, and would benefit from active on-line monitoring of reagents or products or both. Nuclear isotope separations depend on careful control of redox chemistry, using reactive species such as hydroxylamine nitrate, HAN, to change the oxidation state of actinides dissolved in aqueous solution. Hence, we describe a spectroscopic method that could be used to monitor HAN reactions in real time. Because its flexibility, the method could be applied to any aqueous species with absorption in the mid infrared.

Vibrational IR spectra is a tool that offers the selectivity required for identifying molecular species as IR absorptions are characteristic and specific to molecular groups. Vibrational spectra can be interpreted to give thermal energies of IR-active compounds, allowing these to be included in chemical kinetic and dynamical models. The QCL-ATR system of the invention provides portability, second-scale time resolution to follow reaction kinetics high spectral resolution, and enhanced sensitivity through high peak power of the excitation laser.

The QCL-ATR system was used to monitor and assay nitrate-nitrite chemistry representative of the process for the production of plutonium-238 for NASA deep space missions. The chemical processing of neptunium-237 targets after irradiation involves a number of steps to separate a) fission products; b) separate the neptunium and plutonium; and c) purification and polishing. This process achieves separation of neptunium and plutonium through redox chemistry and selective liquid-liquid extraction from nitric acid solution (where the target is dissolved) in a tributyl phosphate (TBP)-organic mixture. Recovery of the plutonium from the organic phase needs introduction of hydroxylamine nitrate ($NH_3OH^+.NO_3^-$) or HAN that is used to reduce Pu(IV) to Pu(III). Hydroxylamine, or HA, is classified as a self-reactive substance. The autocatalytic reaction scheme that takes place in nitric acid solution is given in Reaction (1), showing the conversion of nitric to nitrous acid, and the decomposition of $NH_3OH^+$, Reaction (2).

(1)

(2)

As Reactions (1) and (2) progress consuming $NH_3OH^+$; in strong nitric acid the amount of $HNO_2$ can increase, causing an uncontrolled reaction that can affect the recovery of the plutonium. Hence, it is important to be able to monitor the processes continuously; but are not possible with offline methods of analysis. Commonly employed methods to perform this analysis involve titration with Griess reagent or inductively coupled plasma mass spectroscopy. Such methods require sample collection at different times of the reaction.

IR spectra of HA species have been observed in the gas phase, as n-ethyl hydroxylamine and hydroxylamine chloride. The reported spectra of hydroxylamine chloride found in the literature shows that hydroxylamine exhibits active absorption behavior with multiple peaks in the regions of ~4 and 7-12 μm, coincident with the spectral region covered by the QCL system utilized in this project. Hence, the QCL spectroscopic method was employed online to observe simultaneously the spectral signatures of $NH_3OH^+$ and $HNO_2$. Algorithms were developed to associate changes in the intensity of specific wavelengths to perform a sensitive and selective analysis.

The QCL system (Daylight Solutions, CA) has four laser modules with wavelength tuning ranges of 3.77-4.49 μm and 6.87-12.50 μm. The QCL sources are broadly tunable, pulsed, and provide peak power of up to 400 mW. The QCL module was operated in a pulsed mode of 500 ns, 100 kHz repetition rate, 5% duty cycle and a scan speed of 0.5 μm/sec. The broadly tunable wavelength range allows the system to cover multiple spectral absorption features or peaks of the chemicals of interest, increasing the sensitivity and selectivity of the method. The outgoing beam from the ATR cell is directed onto an MCT detector from VIGO systems Ozaraw Mazowiecki, Poland model PCI-3TE. The MCT is a compact three stage thermoelectrically cooled detector optimized to provide high performance in the spectral range from 2 to 13 μm, $D^* \geq 4.5 \times 10^8$ at $\lambda_{opt}$. The detector converts the laser light to an electrical signal with corresponding amplitude per wavelength, this is the QCL power profile used as background. In the presence of the chemicals species, changes in signal amplitude per wavelength of the QCL gives a characteristic absorption spectrum of each analyte, and therefore gives a definitive fingerprint for molecular identification. Using this prototype, chemical identification is performed by the attenuation at specific wavelengths of the QCL IR beam coming out of the ATR cell.

A LabVIEW interface communicates with the QCL module to control the start/stop of the wavelength scan, data collection, display and storage. The data is collected using the multifunctional data acquisition NI USB-6251 BNC from National Instruments. The laser module sends a trigger pulse to the DAQ board to begin data capture of each wavelength scan. The start and stop of each scan is determined by the time required for each laser module to tune through its wavelength range. As the QCL emits tuning wavelengths, the LabVIEW interface collects the output voltage from the detector as a function of time. The output voltage of the detector is directly related to the intensity or attenuation of the QCL source per wavelength. The LabVIEW interface uses a Fourier transform to extract the spectral information from the data collected as a function of time. The total time from start to end to acquire one spectrum is about 45 seconds with a resolution of 0.6 to 2 nm. The spectral resolution of this system is 3 orders of magnitude better than reported systems for online FTIR spectroscopy.

As the invention is a spectroscopic technique using an ATR liquid cell, a modified Beer-Lambert law can explain the specific wavelength absorption behavior from such system;

$$A = \varepsilon c b', \quad \text{eq. 1}$$

where, A is the absorbance, E is the molar absorptivity, and b' is the effective path length. For ATR-FTIR spectroscopy, the effective path length is equal to the number of reflections of the QCL beam in the ATR crystal times the penetration depth.

$$b' = N d_p, \quad \text{eq. 2}$$

Figure 3:
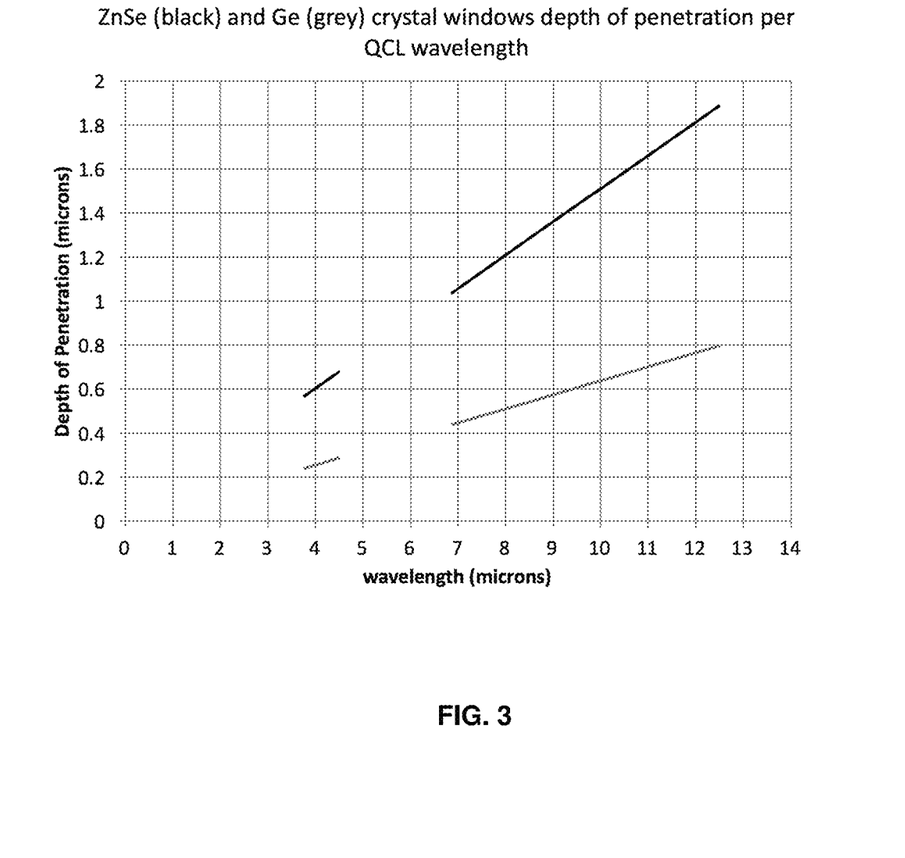
FIG. 3 is a graph showing the calculated penetration depth of the QCL wavelength regions, 3.77-12.50 microns for ZnSe and Ge windows.

In equation 2, N is defined as the number of reflections and $d_p$ is the penetration depth at each reflection per wavelength. The penetration depth of the QCL beam is defined as, $$d_p = \frac{\lambda_1}{2\pi n_1 [\sin^2\theta - n_{21}^2]^{1/2}}, \quad \text{eq. 3}$$

where $n_1$ is the index of refraction of the crystal, $n_2$ is the index of refraction of the sample medium in contact with the crystal, $n_{21}$ equal to $n_2/n_1$ and $\lambda_1 = \lambda_{vaccum}/n_1$. Both two and four mm thick germanium windows were used in this experiment. Figure, shows the penetration depth of our system, for a wavelength range of 3.77-12.50 microns for the ZnSe and Ge windows respectively. To analyze the spectral data, five individual wavelength scans of each sample were taken for averaging. Using the average value, the transmission of the sample was corrected for matrix absorption, $I/I_o$, where $I_o$ is the transmittance of water (blank) and I is the uncorrected transmittance of the sample. From the corrected transmittance value, the absorption is calculated by, $$A = -\log\frac{I}{I_o}, \quad \text{eq. 4}$$

The absorption value is used to build a calibration curve for analytes of interest, such as hydroxyl amine nitrate, using characteristic peak heights at various concentrations. To calculate the standard deviation on absorption, a total of 5 ratios of the blank individual scans were used to calculate absorption values using equation 4. The standard deviation value from the blank at the peak absorption wavelength was then used to calculate the limit of detection (LOD) and the limit of quantification (LOQ) according to IUPAC. The LOD and LOQ are defined as 3.3 σ/m and 10 σ/m, respectively, where σ is the standard deviation and m is the slope of the calibration curve. It has been reported that for hydroxylamine, the vibrational spectra have absorption peaks of interest in the wavelength region covered by our ATR-QCL system, including: The N—OH stretch at 9.7 μm, the $NO_3$ peak stretch at 7.4 μm, and the N—H stretch at 3.778-4.1 μm. Table 1 shows the corresponding calculated values of LOD and LOQ, in grams per liter, for the hydroxylamine nitrate system using the ATR-QCL prototype.

TABLE 1

| Wavelength (pm) | peak | LOD (g/L) | LOQ (g/L) |
|---|---|---|---|
| 3.778 | $OH/NH_3$ | 0.5-1.14 | 3.45 |
| 7.467 | $NO_3$ | 0.31-0.634 | 2.11 |
| 9.754 | N—OH | 1.5-2.94 | 9.81 |

Figure 4:
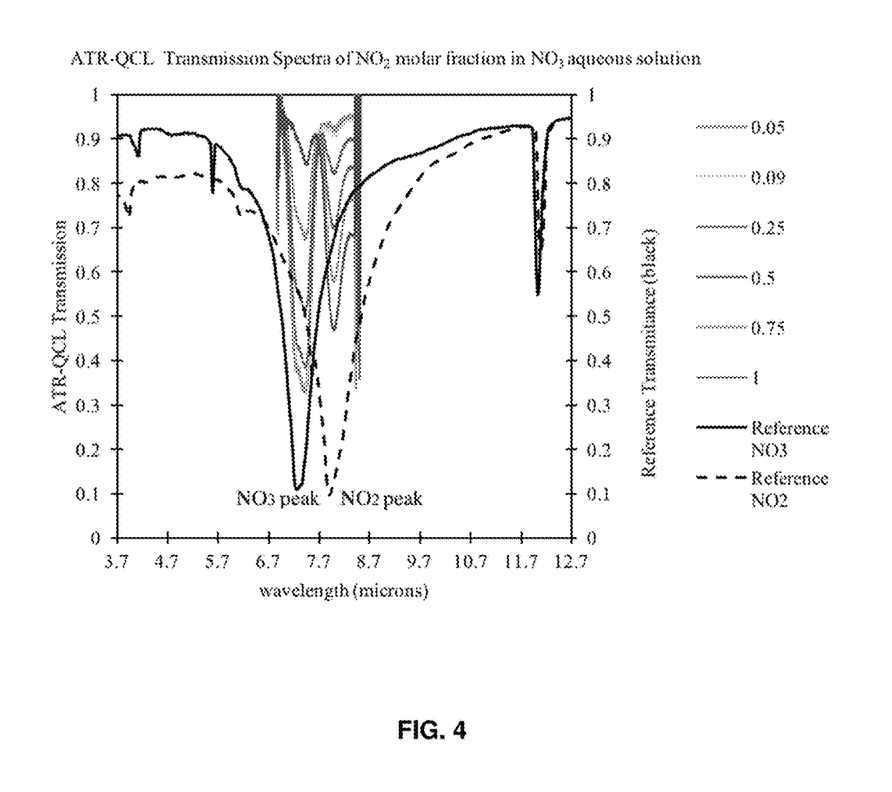
FIG. 4 is a graph showing ATR-QCL Transmission spectra of nitrite molar fraction range of 0.05-1 in presence of nitrate 1M solution. The black lines represent the reference spectra of nitrate (solid) and nitrite (dashed) downloaded from NIST. The isobestic point at about 7.7 microns is well reproduced in the experimental data.

For proof of principle of molecular species detection in high concentration nitrate, we studied the infrared absorption of the aqueous chemical system of $NaNO_2$ in the presence of $NaNO_3$. Spectra of different concentrations of $NaNO_2$ were collected using the QCL-ATR prototype, and are shown in FIG. 4. For this test the concentration range of $NaNO_2$ in $NaNO_3$ was varied from 0.05 to 1 molar fraction. For comparison, reference spectra downloaded from the database of the National Institute of Standards and Technology (NIST) are also plotted in FIG. 4. The absorption peaks from both spectra, reference and experimental, correlate very well, although the isobestic point is shifted from 7.60 to 7.65 μm with the QCL system. Regression analysis gave a linear correlation between peak height and concentration, as well as peak area and concentration. The changes in transmission at specific wavelengths are related to the changes in concentrations in the flow cell. This confirms the capability of the ATR-QCL system to identify multiple species in a chemical system at different concentrations.

Figure 5:
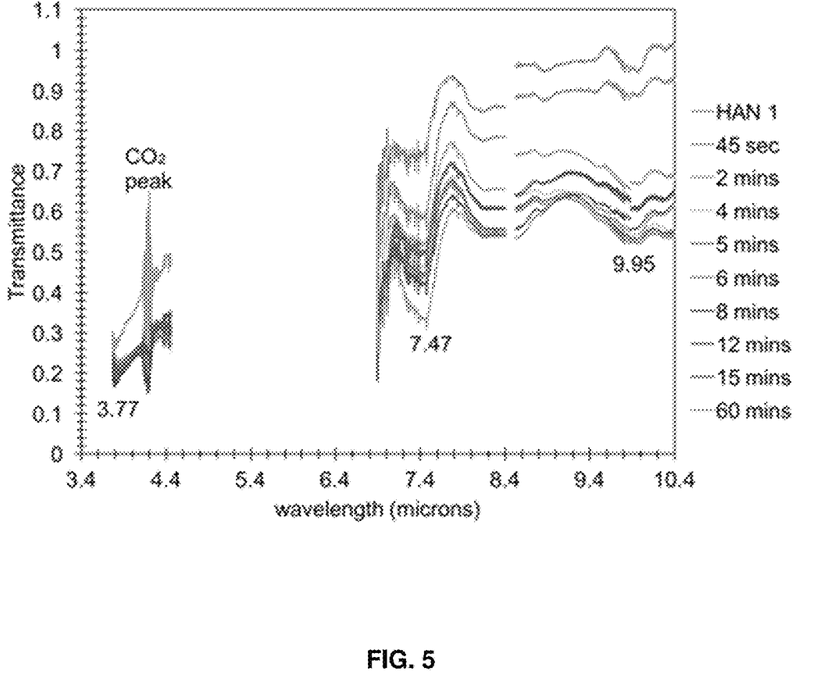
FIG. 5 is a graph showing ATR-QCL transmission spectra of the reaction at 80° C. of HAN 1M and $HNO_3$ 4M aqueous solution. Three distinct absorption peaks are observed associated with HAN molecule reaction with HNO3. The three absorption peaks are indicated in the spectra.

To demonstrate the capability of the system to monitor reactions real time, the reaction between hydroxylamine nitrate and nitric acid was studied. These species will react quickly at high acid concentrations and at high temperatures. In one configuration, 2 mL of HAN 1M as placed directly on the ATR work plate preheated to 80° C., FIG. 5. Nitric acid was added to the plate via pipette (0.5 mL of 4 M $HNO_3$) and the spectrum was monitored over time as the system reacted. As can be seen in FIG. 5, the greatest changes in transmission occur within the first six minutes of the reaction, suggesting that beyond that point, changes could be mainly attributed to evaporation from the ATR trough.

The tests were repeated in a flowing system as described earlier, involving 200 mL total volume of reagents, with the nitric acid being added to the hydroxylamine nitrate at the start of the experiment. FIG. 5 shows the results of the latter test, with the spectra normalized to water taken under the same conditions. First a spectrum of HAN 1M solution was taken, to compare changes in its absorption behavior before the $HNO_3$ was added to the work plate cell. After HAN spectra spectrum was taken, wavelength scans for the reaction mixture were taken every 45 seconds up to an hour. Changes in the spectra observed at specific wavelengths, associated with the N—H and N—O bonds of the HAN molecule indicate changes in HAN concentration.

Figure 6:
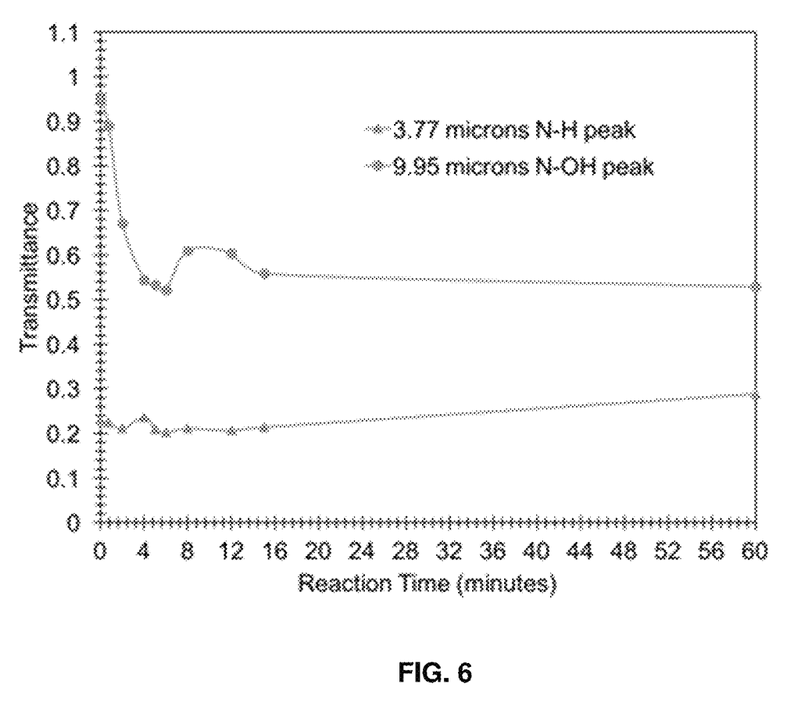
FIG. 6 is a graph showing the ATR-QCL single wavelength, peak height, infrared transmission of the reaction at 80° C. of HAN 1M and $HNO_3$ 4M aqueous solution.

FIG. 6 shows peak height for the feature at 9.95 microns and 3.77 microns where N—OH and N—H absorb respectively. The stronger 9.95 microns feature decreases as a function of time until the $6^{th}$ minute into the reaction due to the dilution of the HAN with the addition of $HNO_3$. After that time, the transmission increases slightly until the $8^{th}$ minute, showing consumption of HAN as it reacts with $HNO_3$. After that, transmission decreases slightly before leveling off to a fairly constant value, indicating that the reaction has finished. Similar behavior can be observed with the feature at 4.2 microns, although a small decrease in transmission can be observed until minute $6^{th}$, after that time the transmission continues to increase until the $60^{th}$ minute, showing a steady reaction. That wavelength region is attributed to the N—H stretch of the amines, directly related to the HAN molecular structure.

The sensitivity of the technique to detect small changes in the spectral region due to changes in the chemical molecular structure has been demonstrated. Single or multiple wavelengths can be used to monitor specific absorption behavior of chemical species as a function of time increasing the selectivity of the method. Because infrared spectroscopy provides specific information about the molecular structure, changes observed are specific to each reagent and product and its concentration. This makes this technique highly selective providing accurate results about the chemical composition of the aqueous system under investigation. In addition, the QCL-ATR configuration provides better resolution than standard methods and sufficient sensitivity to detect chemicals in water.

The invention provides a new approach for high sensitivity and real-time online measurements to monitor chemical processes in aqueous systems. We have demonstrated rapid and continuous sampling, analysis and high sensitivity to detect and identify chemical species in aqueous and organic reactive systems using mid infrared (Mid-IR) external cavity quantum cascade laser (QCL) high-resolution spectroscopy. The system is capable of detecting and identifying the chemicals of interest at low concentrations in aqueous and organic solution with high sensitivity and selectivity, offered by the Mid-IR QCL. The new system provides wide dynamic range, portability, flexibility, and can be deployable at a location close to a shielded chemical reactor or "hot cell".

The invention provides for high sensitivity and real-time online measurements to monitor the kinetics in the processing of nuclear materials and other chemical reactions. Unlike current analytical methods, in this standoff or off-set method, the collection of a sample for analysis is not required. The invention can be used to detect and identify chemical changes and be deployed in hostile environments, radiological or chemical. These include for example nitrate/nitrite analysis related to the separation of Np and Pu for Pu-238 production.

The invention provides high sensitivity and real-time online measurements to monitor the kinetics in the processing of nuclear materials and also many other chemical reactions. Mid infrared (Mid-IR) quantum cascade laser (QCL) high-resolution spectroscopy can be used for rapid and continuous sampling of aqueous and organic reactive systems, using pattern recognition analysis and high sensitivity to detect and identify chemical species. The invention utilizes optical spectroscopy such as Mid-IR QCL spectroscopy for the first time in the detection and identification of ongoing chemical processes in aqueous and organic solution with second-scale time resolution. Unlike current analytical methods, in this standoff or off-set method, the collection of a sample for analysis is not required. Attenuated total reflection (ATR) coupled with the QCL beam can be used to detect and identify chemical changes and be deployed in hostile environments, radiological or chemical. The target nitrate/nitrite analysis related to the separation of Np and Pu for Pu-238 production was demonstrated, and the invention could be also useful for environmental monitoring, processing of biomaterials, and Department of Homeland Security applications.

Vibrational infrared (IR) spectra offer one of the most selective techniques for identifying molecular species as IR absorptions are characteristic and specific to molecular groups, particularly with the high resolution inherent in QCL detection. Traditionally, IR is not utilized to characterize aqueous solutions because of the absorption of $H_2O$, but advances in Mid-IR FTIR make it available for aqueous solution chemistry. The same principle of minimizing matrix absorption by using attenuated total reflection (ATR) was employed here. Advantages of the QCL system over an FTIR include: portability, second-scale time resolution to follow reaction kinetics, high resolution, and enhanced sensitivity through high peak power of the excitation.

The optical spectroscopy device can be a new method of in-situ or online measurement in aqueous solution, which can be used in combination with UV-Visible. The prototype can be incorporated into the reaction system for continuous monitoring and of the reaction progress to provide quantitative and qualitative analysis.

The apparatus can be deployed in reactor systems to monitor chemical reactions related to industries such as but not limited to water treatment facilities, pharmaceuticals, biofuels, and nuclear. Water quality is of concern to all aspects of petroleum production, from drilling, completion, hydraulic fracturing, and production. Drilling muds (aqueous or organic based). These muds are reused on site and there are remediation methods (such as removing fines) between cycles. The muds must be of the correct chemistry and non-removable sediments can be a problem. This QCL-ATR measurement technology (if hardened to an industrial environment) could be applied to on-site processing of drilling muds. Drilling and completion of a well is fraught because of changes in phase (gas versus liquids) that can occur in "plug" flow. (Hence the requirement for a "blow-out" preventor for well safety). The liquid can be hydrocarbon or water. The gas can be methane (or ethane) or H2S—serious safety hazards if not expected. An on-site analysis of the fluid (including gas phase) composition (perhaps even downhole) will allow better control of conditions before a catastrophe happens. Hydraulic fracturing fluid is reused on site several times. Its composition changes each time, with additional loadings of total dissolved solids, hydrocarbons, and sediments/fines. While fracking is robust to chloride, other anions, such as sulfates and carbonates, can cause corrosion, scale formation, and even bacterial growth (that also causes corrosion). Monitoring of fracking fluid would allow better control of fracking conditions, reduced chemical use (e.g., biocides), or perhaps more chemical use (e.g., biocides to prevent corrosion). The fluid properties are of importance throughout the cycle, e.g., hydration, gelation (to obtain the correct viscosity), mixing, etc.

Once the well is in production, fluids are generated in plug flow, the phase fractions of which need to be monitored. Rather than a temporary deployment at the well head, a long-term optical spectroscopy device such as, QCL-ATR monitoring system, could be set up in a pipeline, a battery, an injection well (for water disposal), or wherever speciation affects process conditions.

We claim:
1. A system for online monitoring of an ongoing chemical reaction in a liquid reactor system comprising a reactor having a reactor inlet and a reactor outlet, the system further comprising:
   a sample liquid conduit in communication with the reactor for receiving a continuously flowing sample liquid side stream taken from the reactor downstream of the reactor inlet and upstream of the reactor outlet, and directing the sample liquid stream to an optical spectroscopy device;

a laser beam source for generating a laser beam, wherein the laser beam source provides a laser beam having a wavelength between 3.7 and 12.5 µm;

wherein the optical spectroscopy device comprises a liquid chamber for receiving the sample liquid stream, and a liquid cell attenuated total reflectance (ATR) device having a crystal, the crystal confining the laser beam and propagating an evanescent wave into the sample liquid in the liquid chamber, wherein an absorption pattern is created by chemicals in the sample stream and an optical spectroscopy signal is generated;

a detector for detecting the optical spectroscopy signal and creating a detection signal responsive to the optical spectroscopy signal;

a device for generating a time signal;

a processor for processing the detection signal to determine the identity and amount of at least one chemical species in the liquid and correlating the time signal with the detection signal; and, a sample liquid stream return conduit in communication with the liquid chamber of the optical spectroscopy device for receiving sample liquid from the liquid chamber and returning the sample liquid to the reactor upstream of the reactor outlet and downstream of the sample conduit.

2. The system of claim 1, wherein the laser beam source comprises a quantum cascade laser (QCL) source.

3. The system of claim 1, wherein the reactor system comprises a radiochemical reactor system.

4. A system for controlling ongoing chemical reactions in reactor system comprising a reactor having a reactor inlet and a reactor outlet, the system further comprising:

a sample liquid conduit in communication with the reactor for receiving a continuously flowing sample liquid side stream taken from the reactor at a sample outlet downstream of the reactor inlet and upstream of the reactor outlet and directing the sample liquid stream to an optical spectroscopy device;

a laser beam source for generating a laser beam wherein the laser beam source provides a laser beam having a wavelength between 3.7 and 12.5 µm;

wherein the optical spectroscopy device comprises a liquid chamber for receiving the sample liquid stream and a liquid cell attenuated total reflectance (ATR) device having a crystal, the crystal confining the laser beam and propagating an evanescent wave into the sample liquid in the liquid chamber, wherein an absorption pattern is created by chemicals in the sample stream and an optical spectroscopy signal is generated;

a detector for detecting the optical spectroscopy signal and creating a detection signal responsive to the optical spectroscopy signal; and, a device for generating a time signal;

a processor for processing the detection signal to determine the identity and amount of at least one chemical species in the sample liquid and correlating the time signal with the detection signal, and generating at least one process control signal responsive to the amount of the at least one chemical species in the reactor system;

a process controller for controlling at least one process control device of the ongoing chemical reaction responsive to the process control signal; and, a sample liquid stream return conduit in communication with the liquid chamber of the optical spectroscopy device for receiving sample liquid from the liquid chamber and returning the sample liquid to the reactor upstream of the reactor outlet and downstream of the sample conduit.

5. The system of claim 4, wherein the laser beam source is a quantum cascade laser.

6. The system of claim 4, wherein the reactor system is part of a radiochemical reactor system.

7. A method for monitoring an ongoing chemical reaction in a reactor system comprising a reactor having a reactor inlet and a reactor outlet, comprising the steps of:

directing a continuously flowing sample liquid side stream taken from the reactor downstream of the reactor inlet and upstream of the reactor outlet to an optical spectroscopy device;

generating a laser beam having a wavelength between 3.7 and 12.5 µm;

wherein the optical spectroscopy device comprises a liquid chamber for receiving the sample liquid stream, and a liquid cell attenuated total reflectance (ATR) device having a crystal, the crystal confining the laser beam and propagating an evanescent wave into the sample liquid in the liquid chamber, wherein an absorption pattern is created by chemicals in the sample stream and an optical spectroscopy signal is generated;

creating with a detector a detection signal responsive to the optical spectroscopy signal;

generating a time signal and correlating the time signal with the detection signal;

directing the detection signal to a processor, and processing the detection signal to determine the identity and amount of at least one chemical species in the liquid system; and, returning the sample liquid stream from the liquid chamber to the reactor upstream of the reactor outlet and downstream of the sample outlet from the reactor.

8. The method of claim 7, wherein the laser beam source comprises a quantum cascade laser (QCL) source.

9. The method of claim 7, wherein the liquid reactor system comprises a radiochemical reactor system.

10. The method of claim 7, wherein the processor processes the identity and amount of the at least on chemical species to generate at least one process control signal.

11. The method of claim 10, further comprising the step of directing the at least one process control signal to a process controller to control at least one process control device of the liquid reactor system.

12. The method of claim 7, wherein the method is continuous.

* * * * *